(12) United States Patent
Belongia et al.

(10) Patent No.: US 7,628,338 B2
(45) Date of Patent: Dec. 8, 2009

(54) REFILL FOR A VOLATILE MATERIAL

(75) Inventors: David C. Belongia, Burlington, WI (US); Jeffrey J. Christianson, Oak Creek, WI (US); Marilyn M. Johnson, Wauwatosa, WI (US); Maciej K. Tasz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 451 days.

(21) Appl. No.: 11/522,641

(22) Filed: Sep. 18, 2006

(65) Prior Publication Data

US 2008/0093475 A1    Apr. 24, 2008

(51) Int. Cl.
*A61L 9/04* (2006.01)

(52) U.S. Cl. .......................... 239/44; 239/34; 239/145; 239/326

(58) Field of Classification Search ............. 239/34, 239/41, 145, 326; 222/187
See application file for complete search history.

(56) References Cited

U.S. PATENT DOCUMENTS

| | | | |
|---|---|---|---|
| 2,474,605 A | 6/1949 | Wheeler et al. | |
| 2,474,607 A * | 6/1949 | Wheeler et al. | 239/47 |
| 3,089,182 A * | 5/1963 | Lofgren | 401/199 |
| 3,091,396 A | 5/1963 | Curtin | |
| 3,345,674 A | 10/1967 | Groft | |
| 4,621,768 A | 11/1986 | Lhoste et al. | |
| 5,647,053 A | 7/1997 | Schroeder et al. | |
| 5,909,845 A | 6/1999 | Greatbatch et al. | |
| 6,236,807 B1 | 5/2001 | Ruffolo et al. | |
| 6,354,513 B1 | 3/2002 | Basaganas Millan | |
| 6,386,781 B1 * | 5/2002 | Gueret | 401/198 |
| 6,446,880 B1 | 9/2002 | Schram | |
| RE38,150 E | 6/2003 | Greatbatch et al. | |
| 6,619,560 B1 | 9/2003 | Chun | |
| 6,706,988 B1 | 3/2004 | Helf et al. | |
| 6,752,327 B2 | 6/2004 | Martens, III et al. | |
| 6,786,427 B2 | 9/2004 | Schram et al. | |
| 6,862,403 B2 | 3/2005 | Pedrotti et al. | |
| 6,896,196 B2 | 5/2005 | Vieira | |
| 6,899,280 B2 | 5/2005 | Kotary et al. | |
| 2002/0136542 A1 * | 9/2002 | He et al. | 392/395 |
| 2004/0262419 A1 | 12/2004 | Kotary et al. | |
| 2006/0016904 A1 | 1/2006 | Caserta | |
| 2006/0163376 A1 | 7/2006 | Lakatos | |

FOREIGN PATENT DOCUMENTS

EP    1103479 A1    5/2001

OTHER PUBLICATIONS

U.S. Appl. No. 11/442,802 filed May 30, 2006.
PCT/US2007/020190 International Search Report and Written Opinion dated Jun. 3, 2008.

* cited by examiner

*Primary Examiner*—Dinh Q Nguyen (57) ABSTRACT

A refill for a volatile material includes a container having a reservoir portion and a neck portion. The refill further includes a plug assembly disposed within the neck portion of the container and a channel through a central portion of the plug assembly. Still further, the refill includes a porous wick extending through the channel, wherein the wick includes an upper portion extending outside the container and a lower portion disposed within the reservoir portion. A slit is formed in the lower portion of the wick to form a barb that catches on the plug assembly to prevent removal of the wick from the container.

18 Claims, 5 Drawing Sheets

REFILL FOR A VOLATILE MATERIAL

CROSS REFERENCE TO RELATED APPLICATIONS

Not applicable.

BACKGROUND OF THE INVENTION

1. Field of the Invention

The present invention relates to refills for volatile materials, and more particularly, to refills for volatile materials and retention mechanisms therefor.

2. Description of the Background of the Invention

Devices that release vapors into the air are well-known in the art. Generally, the purpose of such devices is to deodorize, disinfect, or add positive fragrance to the ambient air, or to distribute insect repellants or insecticides into the air to kill or repel unwanted pests, such as mosquitoes and gnats.

Various types of devices have been employed to dispense vapors into the air. For example, passive dispensing devices are known, wherein a volatile material in a gel, liquid, or solid form is provided within a container. The volatile material is diffused into the surrounding atmosphere, and the diffusion may be assisted by the natural airflow within the surroundings. A vent may be included in such passive dispensing devices to increase and decrease the amount of volatile material emitted from the passive dispensing devices. Aerosol containers have also been employed to eject droplets of volatile material from a pressurized container into a surrounding atmosphere upon activation of a trigger.

Other devices have utilized mechanical or electrical devices to disperse volatile materials into the atmosphere. In one such device, a container having a porous wick disposed therein in contact with a liquid volatile material and extending out a neck of the container is disposed within a diffusion device. The volatile material travels through the porous wick to an exposed end thereof. The diffusion device may include a heater and/or a fan disposed adjacent the exposed end of the wick to assist in the volatilization and/or dispersion of the liquid volatile material in the wick.

Containers having wicks in contact with a volatile material generally include a reservoir portion for holding the volatile material and a neck portion that forms an opening in communication with the reservoir portion. A neck closure or plug is disposed within the neck portion, wherein the neck closure includes a hole through a central portion thereof. Various devices have been utilized to secure the wick within the neck closure. One such device includes sectors formed in the neck closure with downwardly extending semi-pyramidal-shaped projections having a triangular outline, wherein the projections extend into and clamp the wick to prevent removal of the wick from the neck closure. Another device comprises a retaining pin that extends through a portion of the wick below the neck closure to prevent removal of the wick through the neck closure. In another embodiment, a cylindrical neck closure is disposed within a neck portion of the container and cylindrical portions of the retaining ring above and/or below the neck portion are crimped to form pressure points on the wick to preclude upward extraction of the wick from the neck closure. Still another device includes an annular groove formed in a lower portion of the wick and a flexible collar disposed within the annular groove. The collar includes opposing wings that help prevent removal of the wick from the container.

SUMMARY OF THE INVENTION

According to one aspect of the present invention, a refill for a volatile material includes a container having a reservoir portion and a neck portion. The refill further includes a plug assembly disposed within the neck portion of the container and a channel through a central portion of the plug assembly. Still further the refill includes a porous wick extending through the channel, wherein the wick includes an upper portion extending outside the container and a lower portion disposed within the reservoir portion. A slit is formed in the lower portion of the wick to form a barb that catches on the plug assembly to prevent removal of the wick from the container.

According to another aspect of the present invention, a refill for a volatile material includes a container having a reservoir portion and a neck portion. The refill further includes a plug assembly disposed within the neck portion of the container and a channel through a central portion of the plug assembly. Still further, the refill includes a porous wick extending through the channel and a retaining ring extending outwardly from a bottom portion of the plug assembly. The retaining ring includes a plurality of flexible fingers extending outwardly therefrom, wherein the flexible fingers allow insertion of the plug assembly through the neck portion of the container but prevent extraction of the plug assembly through sane.

According to yet another aspect of the present invention, a refill for a volatile material includes a container having a reservoir portion and a neck portion. The refill further includes a plug assembly disposed within the neck portion of the container and a channel through a central portion of the plug assembly. A porous wick extends through the channel, wherein the wick includes an upper portion extending outside the container and a lower portion disposed within the reservoir portion. A slit is formed in the lower portion of the wick, wherein the slit forms a barb that catches on the plug assembly to prevent removal of the wick from the container. A retaining ring extends outwardly from a bottom portion of the plug assembly, wherein the retaining ring prevents extraction of the plug assembly through the neck portion.

Other aspects and advantages of the present invention will become apparent upon consideration of the following detailed description.

BRIEF DESCRIPTION OF THE DRAWINGS

Throughout the figures, like or corresponding reference numerals have been used for like or corresponding parts.

DETAILED DESCRIPTION OF THE PREFERRED EMBODIMENTS

Figure 1:
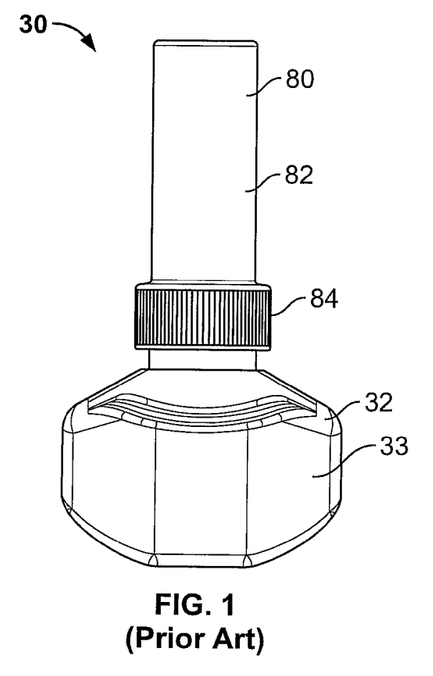
FIG. 1 is a front elevational view of a refill for a volatile material.
Figure 2:
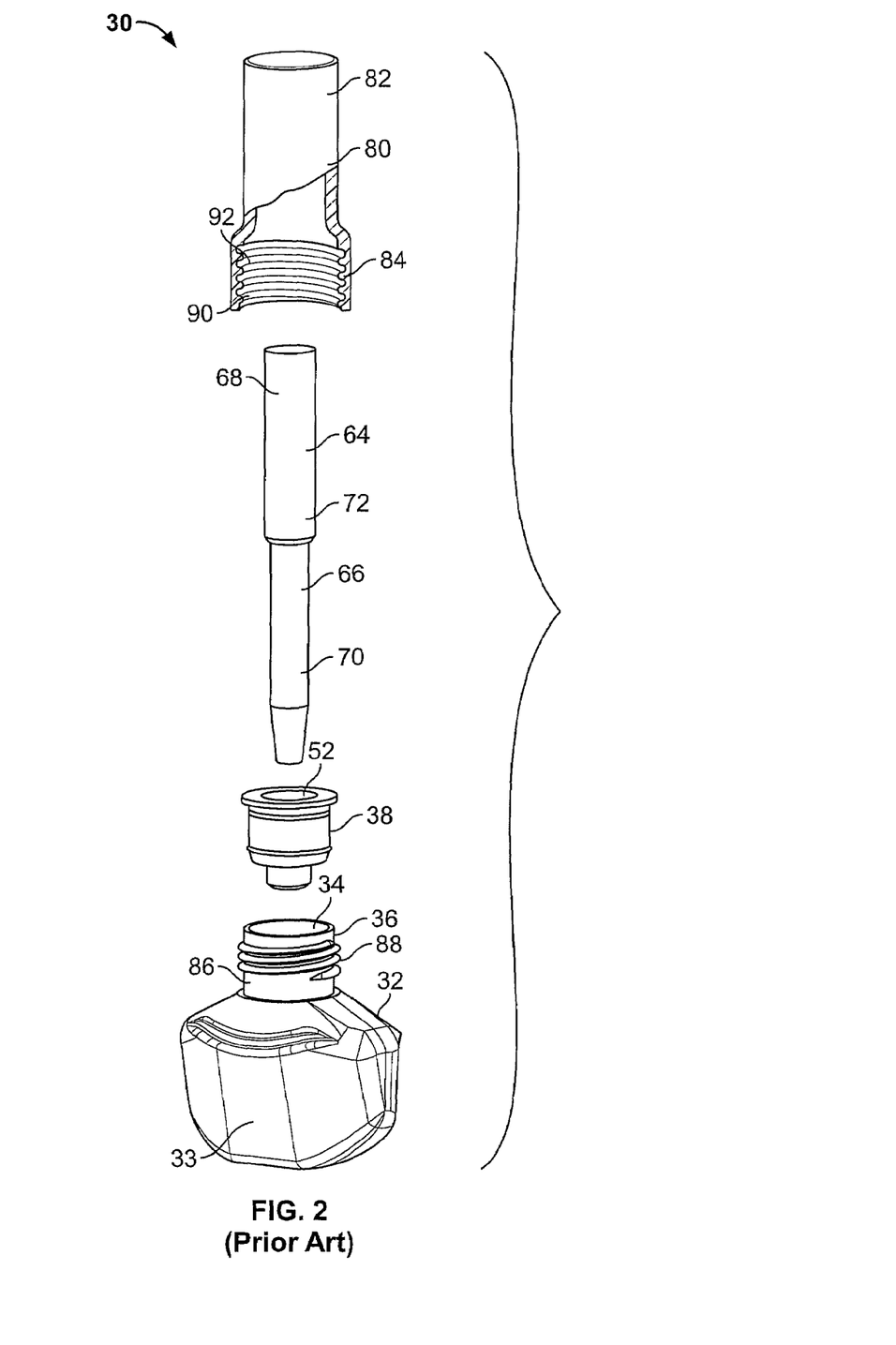
FIG. 2 is an exploded top isometric view of the refill of FIG. 1 with a partial cutaway of an overcap thereof to show threading in the overcap.
Figure 3:
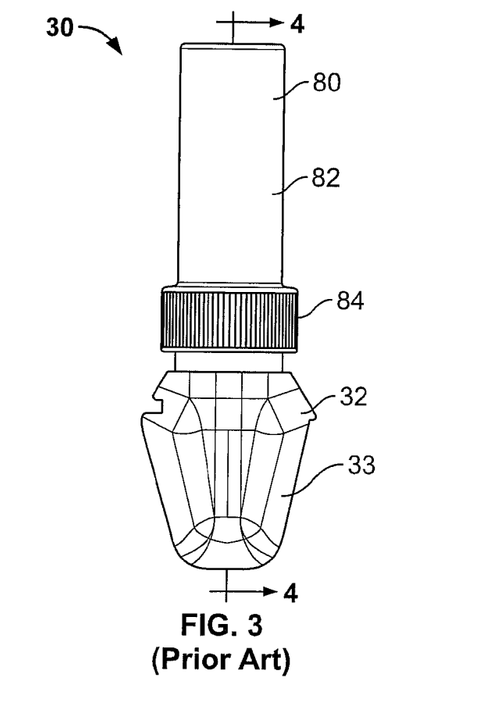
FIG. 3 is a side elevational view of the refill of FIG. 1.

As depicted in FIGS. 1-3, a refill for a volatile material 30 includes a container 32 having a volatile material disposed within a reservoir portion 33 of the container 32. The volatile material is preferably in liquid form and is preferably a fragrance. Alternatively, the volatile material may be an insecticide, an insect repellant, an insect attractant, a disinfectant, a sanitizer, an air purifier, an aromatherapy scent, an antiseptic, an odor eliminator, an air freshener, a deodorizer, or any other volatile material(s) that are usefully dispersed into the air.

Figure 4:
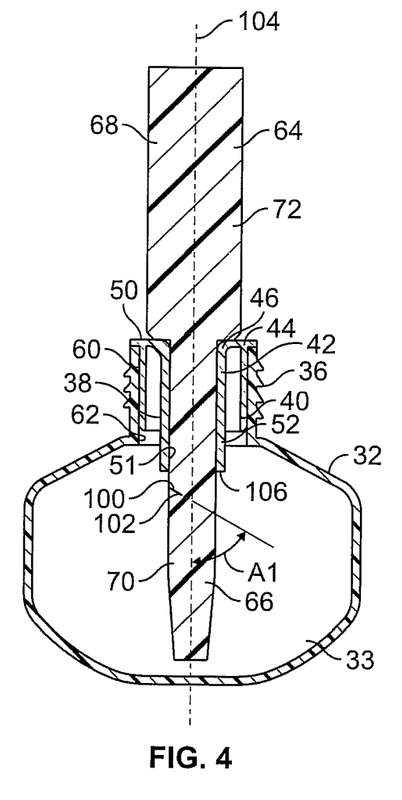
FIG. 4 is a cross-sectional view of the refill of FIG. 1 taken generally along the lines 4-4 of FIG. 3 and with the overcap removed and incorporating a first embodiment of a retention mechanism.
Figure 5:
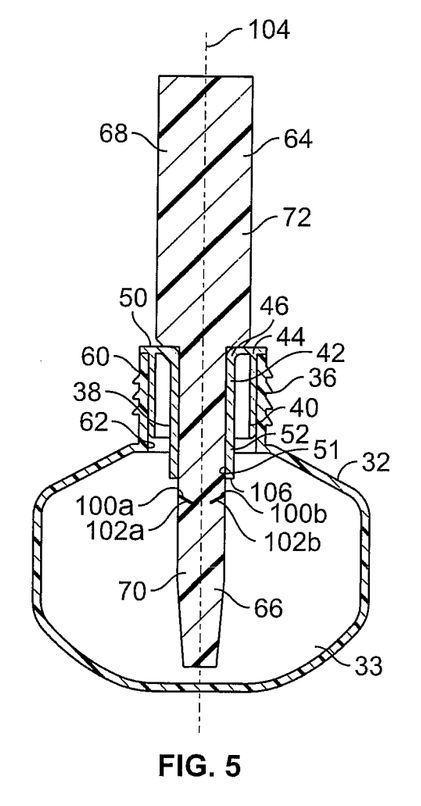
FIG. 5 is a cross-sectional view similar to FIG. 4 incorporating a second embodiment of a retention mechanism.
Figure 6:
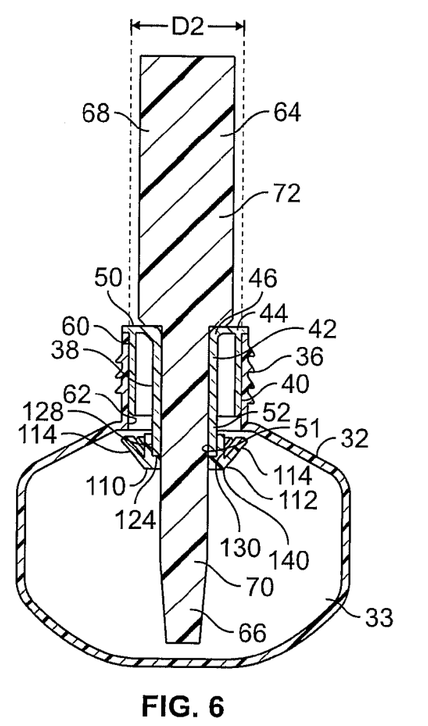
FIG. 6 is a cross-sectional view similar to FIG. 4 incorporating a third embodiment of a retention mechanism.

The container 32 is preferably, although not necessarily, made of a translucent plastic material. The container 32 includes an opening 34 forming a neck portion 36 of the container 32, wherein a plug assembly 38 is inserted into and secured in the neck portion 36. Referring to FIGS. 4-6, the plug assembly 38 includes an outer cylindrical wall 40 and an inner cylindrical wall 42 joined at end portions 44, 46, respectively, thereof by an annular radial planar member 50. An inner surface 51 of the inner cylindrical wall 42 defines a bore 52 that extends fully through the plug assembly 38. The plug assembly 38 is sized such that an outer surface 60 of the outer cylindrical wall 40 and an inner surface 62 of the neck portion 36 define an interference fit therebetween when the plug assembly 38 is placed into the neck portion 36 to retain the former in the latter. Optionally, the plug assembly 38 may be retained on the neck portion 36 by a threaded connection, wherein the outer surface 60 of the outer cylindrical wall 40 and the inner surface 62 of the neck portion 36 include threads so the plug assembly 38 may be threaded into the neck portion 36. The plug assembly 38 may include vents (not shown) through the annular radial planar member 50 to allow air to enter and escape the reservoir portion 33 of the container 32.

A porous wick 64 is disposed within the channel 52 such that a lower portion 66 of the wick 64 extends into the reservoir portion 33 in contact with the volatile material and an upper portion 68 of the wick 64 extends out of the container 32 and in contact with ambient air. The wick 64 serves to transport the volatile material in the reservoir portion 33 from the reservoir portion 33 to the upper portion 68 of the wick 64, wherein the upper portion 68 serves to disperse the volatile material into the ambient air.

In the refill of FIGS. 1-3, the wick 64 includes a first portion 70 having a first diameter and a second portion 72 having a second diameter, wherein the first diameter is less than the second diameter. Optionally, the first and second diameters may be the same or the first diameter may be greater than the second diameter. The wick 64 is formed from a plastic material such as nylon, ultra high molecular weight high density polyethylene, or high density polypropylene. Optionally, the first and second portions 70, 72 of the wick 64 may be formed of different materials to create portions 70, 72 with different properties. More generally, the wick 64 may have any number of portions of different or identical materials and/or dimensions and/or shapes, or a combination of different and identical materials, dimensions, and/or shapes, as desired As seen in FIGS. 1-3, the refill 30 further includes an overcap 80 that is disposed over the wick 64 when the refill 30 is not in use. The overcap 80 includes an upper cylindrical portion 82 and a lower cylindrical portion 84. Referring to FIG. 1, an outer surface 86 of the neck portion 36 of the container 32 includes threads 88. An inner surface 90 of the lower cylindrical portion 84 of the overcap 80 includes corresponding threads 92 that engage the threads 88 of the neck portion 36 to allow the overcap 80 to be screwed onto the neck portion 36 of the container 32 to create a closure between the container 32 and the overcap 80.

A first embodiment of a retention mechanism of the present invention is depicted in FIG. 4. The retention mechanism is implemented within the refill 30 of FIGS. 1-3 and includes a single slit 100 disposed in the lower portion 66 of the wick 64 below the plug assembly 38, wherein the slit 100 creates a barb 102. In any of the embodiments described herein, prior to or after insertion into the plug assembly 38, the barb 102 may be deformed outwardly to ensure that an interference is defined between the barb 102 and the plug assembly 38. In use, if a user attempts to extract the wick 64 from the plug assembly 38, the barb 102 catches on a lower portion 106 of the plug assembly 38, thereby preventing removal of the wick 64 from the plug assembly 38. If enough pressure is exerted on the wick 64, the wick 64 may also break at an area adjacent the barb 102. The slit 100 is angled downwardly and inwardly at an angle and at a depth that prevents the barb 102 from breaking off due to shear forces on the barb 102 created upon an attempt to remove the wick 64 so that the barb 102 prevents removal of the wick 64. In particular, the slit 100 is formed at an angle A1 (FIG. 4) with respect to a longitudinal axis 104 of the wick 64, wherein A1 is preferably between about 30 degrees and about 80 degrees, more preferably between about 55 degrees and about 65 degrees, and most preferably about 60 degrees. The slit 100 is also formed at a depth perpendicular to the longitudinal axis 104, wherein the depth is preferably between about 0.060 inch (1.52 mm) and about 0.125 inch (3.18 mm), more preferably between about 0.075 inch (1.91 mm) and about 0.085 inch (2.16 mm), and most preferably about 0.100 inch (2.54 mm).

FIG. 5 depicts a second embodiment of a retention mechanism of the present invention. The retention mechanism is implemented within the refill 30 of FIGS. 1-3 and includes two slits 100a, 100b disposed in the lower portion 66 of the wick 64, below the plug assembly 38, wherein the slits 100a, 100b create corresponding barbs 102a, 102b. Preferably, the slits 100a, 100b are disposed on diametrically opposite sides of the wick 64 opposite one another, although this need not be the case. Optionally, one of the slits 100a, 100b may be disposed above or below the other slit 100a, 100b along the longitudinal axis 104 of the wick 64. In fact, in any of the embodiments disclosed herein, any number of slits may be made in the wick 64 to form any number of barbs 102 at any locations on the wick 64, as desired, provided that the wick 64 is not unduly weakened by such slits. As with the embodiment of FIG. 4, if a user attempts to extract the wick 64 from the plug assembly 38, the barbs 102a, 102b catch on the lower portion 106 of the plug assembly 38, thereby preventing removal of the wick 64 from the plug assembly 38. If the pressure exerted on the wick 64 is great enough, the wick 64 may break at an area between the barbs 102a, 102b. In order to minimize such possibility, the slits 100a, 100b are preferably both formed at an angle similar to the slit 100 of FIG. 4 and are preferably both formed at the same angle. Optionally, the slits 100a, 100b may be formed at different angles within the ranges detailed above with respect to the embodiment of FIG. 4. The slits 100a, 100b are formed at a depth perpendicular to the longitudinal axis 104, wherein the depth is preferably between about 0.060 inch (1.52 mm) and about 0.125 inch (3.18 mm), more preferably between about 0.075 inch (1.91 mm) and about 0.085 inch (2.16 mm), and most preferably about 0.080 inch (2.03 mm).

Figure 8:
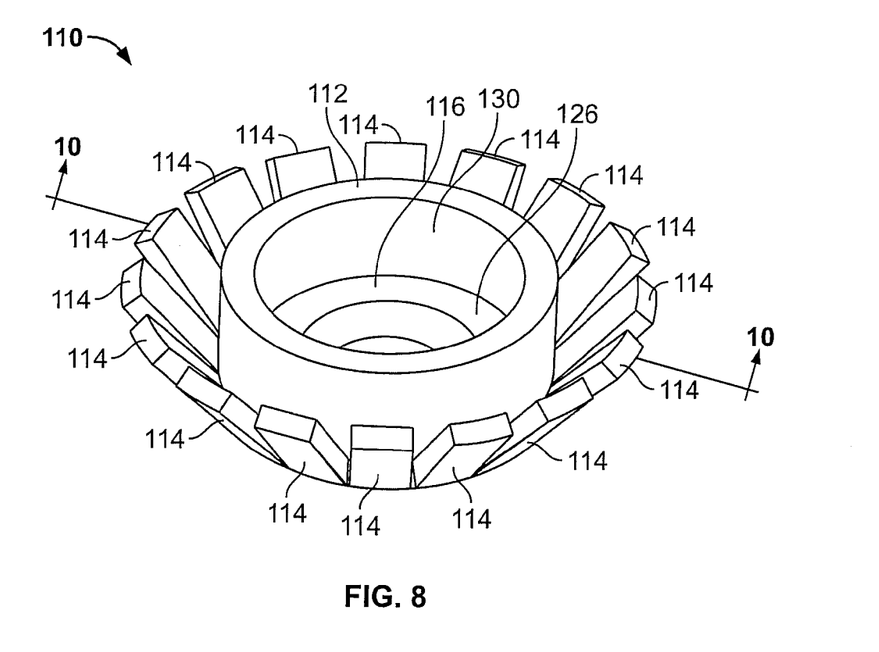
FIG. 8 is a top isometric view of a retaining ring of FIGS. 6 and 7.
Figure 9:
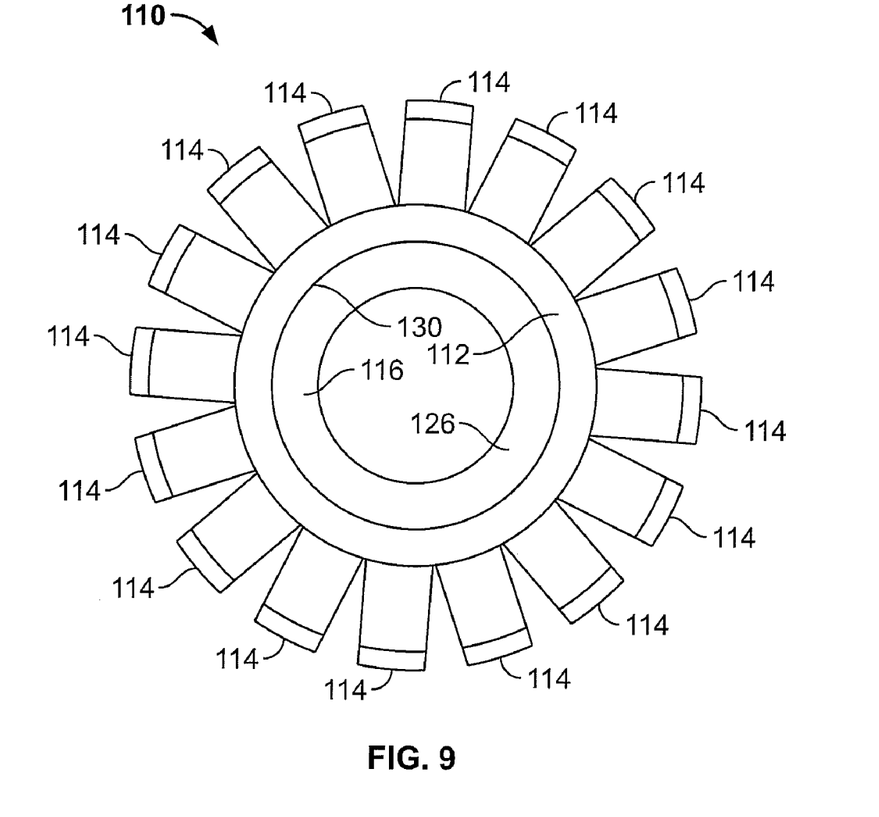
FIG. 9 is a plan view of the retaining ring of FIGS. 6 and 7.
Figure 10:
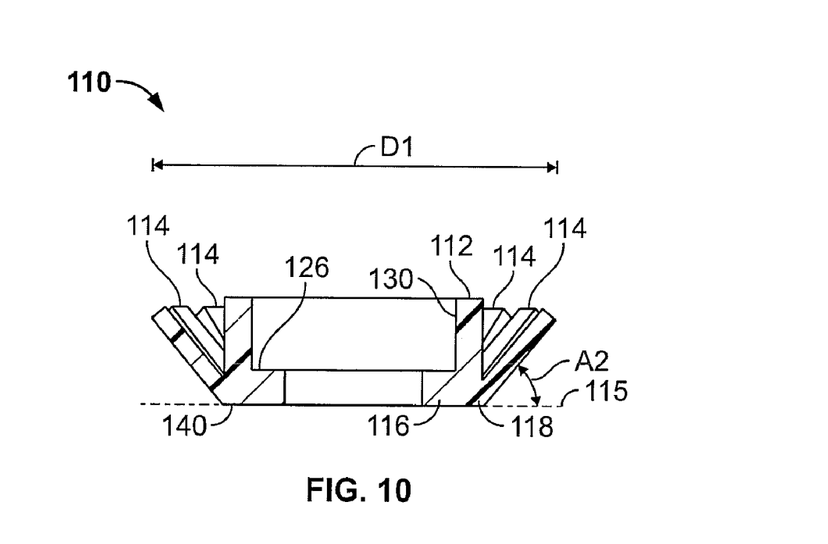
FIG. 10 is a cross-sectional view of the retaining ring of FIGS. 6 and 7 taken generally along the lines 10-10 of FIG. 8.

A third embodiment of a retention mechanism of the present invention is shown in FIG. 6. The retention mechanism is employed within the refill 30 of FIGS. 1-3. As best seen in FIGS. 8-10, the retention mechanism includes a retaining ring 110 having an annular member 112 and a plurality of flexible fingers 114 integral with and extending upwardly and outwardly from the annular member 112. The retaining ring 110 also includes an inner annular member 116 that extends inwardly from the annular member 112 at a lower portion 118 of the annular member 112. The retaining ring 110 is preferably, although not necessarily, permanently secured to or integral with the inner cylindrical wall 42 of the plug assembly 38 such that a lower surface 124 of the inner cylindrical wall 42 of the plug assembly 38 is adjacent an upper surface 126 of the inner annular member 116 and an outer surface 128 of the inner cylindrical wall 42 is adjacent an inner surface 130 of the annular member 112. If the retaining ring 110 is secured to inner cylindrical wall 42, any adhesive or means for joining two components may be utilized to secure the retaining ring 110 and inner cylindrical wall 42 to one another. Preferably, although not necessarily, the plug assembly 38 and the retaining ring 110 are both made of a plastic material, such as for example, high density polyethylene (HDPE) or polypropylene (PP). Also, the plug assembly 38 and the retaining ring 110 are preferably the same material to aid in joining the components or to aid in forming a single integral component.

During assembly of the refill 30 and the retention mechanism of FIG. 6, the wick 64 is inserted into the joined plug assembly 38 and retaining ring 110 and thereafter the plug assembly 38, the retaining ring 110, and the wick 64 are inserted through the neck portion 36 of the container 32. The flexible fingers 114 flex inwardly toward the longitudinal axis 104 of the wick 64 as the plug assembly 38, the retaining ring 110, and the wick 64 are inserted through the neck portion 36 of the container 32 and the flexible fingers 114 expand outwardly as soon as the fingers 114 pass from the neck portion 36 into the reservoir portion 33 of the container 32 (i.e., as soon as the fingers 114 clear the bore 52 of the neck portion 36). The fingers 114 expand outwardly such that the retaining ring 110 with expanded fingers 114 has a diameter D1 (FIG. 10) that is greater than an inner diameter D2 (FIGS. 6 and 7) of the bore 52 of the neck portion 36, thereby preventing removal of the plug assembly 38 and the retaining ring 110 from the container 32. The fingers 114 are disposed at an angle A2 from a lateral axis 115 (FIG. 10) in an expanded position, wherein the lateral axis 115 is aligned with a lower edge 140 of the retaining ring 110. Preferably, the angle A2 is between about 30 degrees and about 80 degrees, more preferably between about 45 degrees and about 55 degrees, and most preferably about 50 degrees.

Although sixteen flexible fingers 114 are depicted, one or more flexible fingers 114 could be utilized to resist removal of the plug assembly 38 from the container 32 and still create balance around a circumference of the retaining ring 114. In an embodiment including one flexible finger, the finger may extend around a large portion or the entire retaining ring 114.

Figure 7:
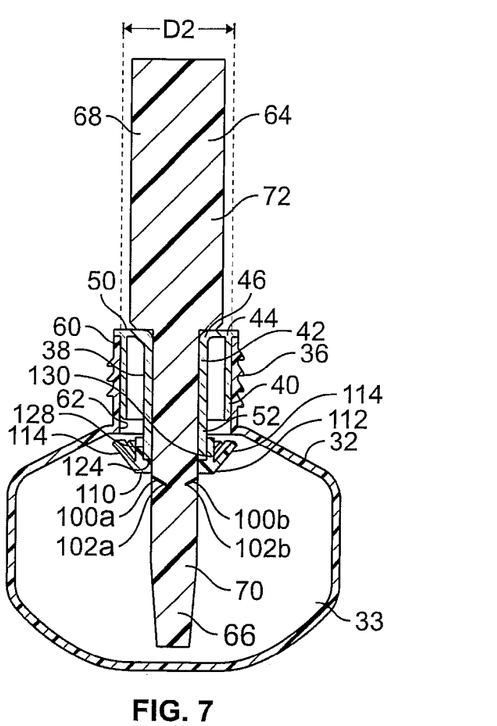
FIG. 7 is a cross-sectional view similar to FIG. 4 incorporating a fourth embodiment of a retention mechanism.

FIG. 7 depicts a fourth embodiment of a retention mechanism of the present invention. The retention mechanism includes one or more slits 100a, 100b disposed in the wick 64 and forming corresponding barbs 102a, 102b, wherein the slit(s) 100a, 100b are discussed in detail above with respect to the first and second embodiments of FIGS. 4 and 5. The retention mechanism of FIG. 7 further includes a retaining ring 110, as discussed in detail above with respect to the third embodiment of FIG. 6. In use, if a user attempts to extract the wick 64 from the plug assembly 38, the barb 102 catches on a lower portion 106 of the plug assembly 38 and/or the retaining ring 110, thereby preventing removal of the wick 64 from the plug assembly 38. The retaining ring 110 prevents removal of the plug assembly 38 from the neck portion 36 of the container 32 that might occur if there is resistance to removal of the wick 64 from the plug assembly 38.

The retention mechanisms as disclosed herein may be employed in any number of refills and may be utilized with any number of diffusion devices. Examples of some of such refills and diffusion devices are disclosed in Schroeder et al. U.S. Pat. No. 5,647,053, issued Jul. 8, 1997, and entitled "Vapor Dispensing Device," Greatbatch et al. U.S. Pat. No. 5,909,845, issued Jun. 8, 1999, and entitled "Wick-based Liquid Emanation System with Child-resistant Overcap," Pedrotti et al. U.S. Pat. No. 6,862,403, issued Mar. 1, 2005, and entitled "Rotatable Plug Assembly Including an Extra Outlet," Helf et al. U.S. Pat. No. 6,706,988, issued Mar. 16, 2004, and entitled "Switch Actuating Mechanism and Electrically Controlled Device Using Same," Martens, III et al. U.S. Pat. No. 6,752,327, issued Jun. 22, 2004, and entitled "Atomizer with Tilted Orifice Plate and Replacement Reservoir for Same," Schram et al. U.S. Pat. No. 6,786,427, issued Sep. 7, 2004, and entitled "Liquid Sealing Arrangements for Replaceable Liquid Reservoirs," and Majerowski et al. U.S. patent application Ser. No. 11/442,802, filed May 30, 2006, and entitled "Passive Dispensing Device," all assigned to the assignee of the present application and the disclosures of which are all hereby incorporated by reference.

INDUSTRIAL APPLICABILITY

The present invention provides various features incorporated into a refill, wherein the features facilitate retention of a wick within a container. Generally, the wick is secured within an opening of the container by a plug assembly, wherein the container holds a volatile material in liquid form. The features described herein prevent removal of the wick from the plug assembly and/or prevent removal of the plug assembly through the container opening.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A refill for a volatile material, comprising:
   a container having a reservoir portion and a neck portion;
   a plug assembly disposed within the neck portion of the container and further including a channel through a central portion of the plug assembly;
   a porous wick extending through the channel;
   a retaining ring extending outwardly from a bottom portion of the plug assembly, wherein the retaining ring prevents extraction of the plug assembly through the neck portion; and
   a slit formed in the wick and disposed below the retaining ring.

2. The refill of claim 1, wherein the retaining ring includes a plurality of flexible fingers extending outwardly therefrom and wherein the flexible fingers allow insertion of the plug assembly through the neck portion but prevent extraction of the plug assembly through the neck portion.

3. The refill of claim 1, wherein the slit is formed at a downward angle of about 60 degrees with respect to a longitudinal axis of the wick to allow the barb to catch on the retaining ring.

4. The refill of claim 3, further including a second slit formed in the wick at a downward angle, wherein the first-named and second slits are disposed in diametrically opposite sides of the wick.

5. The refill of claim 1, wherein the flexible fingers extend outwardly and upwardly toward a top portion of the container at an angle of about 50 degrees from a lateral axis aligned with a lower edge of the retaining ring.

6. The refill of claim 1, wherein the retaining ring is secured to the plug assembly.

7. The refill of claim 6, wherein the retaining ring is integral with the plug assembly.

8. A refill for a volatile material, comprising:
   a container having a reservoir portion and a neck portion;
   a plug assembly disposed within the neck portion of the container and having an inner cylindrical wall;
   a porous wick extending through the plug assembly into the reservoir portion of the container;
   a slit formed iii a lower portion of the wick, wherein the slit forms a barb that catches on the plug assembly to prevent removal of the wick from the container; and
   a retaining ring having an annular member coextensive and integral with the inner cylindrical wall of the plug assembly, wherein the retaining ring extends outwardly and upwardly into the reservoir portion and prevents extraction of the plug assembly through the neck portion.

9. The refill of claim 8, wherein the retaining ring further includes an inner annular member extending inwardly from a portion of the annular member.

10. The refill of claim 9, wherein the inner cylindrical wall of the plug assembly further includes a lower surface disposed adjacent an upper surface of the inner annular portion and an outer surface of the inner cylindrical wall is disposed adjacent an inner surface of the annular member.

11. The refill of claim 8, wherein the retaining ring further includes a plurality of flexible fingers extending upwardly and outwardly from the annular member.

12. The refill of claim 11, wherein the plurality of flexible fingers extend outwardly and upwardly at an angle of about 50 degrees from a lateral axis aligned with a lower edge of the retaining ring.

13. The refill of claim 8, wherein the slit is formed in the wick at a downward angle.

14. A refill for a volatile material, comprising:
   a container having a reservoir portion and a neck portion;
   a plug assembly disposed within the neck portion of the container and further including a channel through a central portion thereof;
   a porous wick extending through the channel;
   a slit formed in a lower portion of the wick; and
   a retaining ring disposed within the reservoir portion and extending outwardly from a bottom portion of the plug assembly, wherein the retaining ring includes an annular member and at least one flexible finger integral with and extending upwardly and outwardly from the annular member.

15. The refill of claim 14, wherein the at least one flexible finger extends toward and contacts a top portion of the container upon attempted removal of the plug assembly from the container.

16. The refill of claim 15, wherein the at least one flexible finger extends upwardly at an angle of about 50 degrees from a lateral axis aligned with a lower edge of the retaining ring.

17. The refill of claim 14, wherein the retaining ring includes a plurality of flexible fingers.

18. The refill of claim 17, wherein the retaining ring includes twelve flexible fingers.

* * * * *

UNITED STATES PATENT AND TRADEMARK OFFICE
CERTIFICATE OF CORRECTION

PATENT NO. : 7,628,338 B2
APPLICATION NO. : 11/522641
DATED : December 8, 2009
INVENTOR(S) : David C. Belongia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Column 7, line 26, replace "iii" with --in--.

Signed and Sealed this

Twenty-sixth Day of October, 2010

David J. Kappos
*Director of the United States Patent and Trademark Office*